(12) United States Patent
Patek et al.

(10) Patent No.: US 12,017,045 B2
(45) Date of Patent: *Jun. 25, 2024

(54) METHOD, SYSTEM, AND COMPUTER READABLE MEDIUM FOR CONTROLLING INSULIN DELIVERY USING RETROSPECTIVE VIRTUAL BASAL RATES

(71) Applicant: UNIVERSITY OF VIRGINIA PATENT FOUNDATION, Charlottesville, VA (US)

(72) Inventors: Stephen D. Patek, Charlottesville, VA (US); Marc D. Breton, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 330 days.

This patent is subject to a terminal disclaimer.

(21) Appl. No.: 17/502,346

(22) Filed: Oct. 15, 2021

(65) Prior Publication Data
US 2022/0040407 A1 Feb. 10, 2022

Related U.S. Application Data

(63) Continuation of application No. 16/483,487, filed as application No. PCT/US2018/016837 on Feb. 5, 2018, now Pat. No. 11,179,517.
(Continued)

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61M 5/14244* (2013.01);
(Continued)

(58) Field of Classification Search
None
See application file for complete search history.

(56) References Cited

U.S. PATENT DOCUMENTS 8,088,098 B2 1/2012 Yodfat et al.
8,732,188 B2 5/2014 Doniger et al.
(Continued)

FOREIGN PATENT DOCUMENTS

CA 2927335 A1 4/2016
CN 101254322 A 9/2008
(Continued)

OTHER PUBLICATIONS

Office Action (Notice of Reasons for Refusal) dated Mar. 29, 2022, by the Japanese Patent Office in corresponding Japanese Patent Application No. 2019-542178, and an English Translation of the Office Action. (11 pages).
(Continued)

*Primary Examiner* — Manuel A Mendez
(74) *Attorney, Agent, or Firm* — BUCHANAN INGERSOLL & ROONEY PC

(57) ABSTRACT

Equivalent insulin pump retrospective virtual basal rates for daily injections are constructed from planned insulin injections according to a virtual basal rate profile developed for a patient, and a database of historical insulin injections, i.e. basal injections actually administered by the patient, providing a unified framework for analysis, design, optimization, and adaptation of MDI (multiple daily injections) and CSII (continuous subcutaneous insulin infusion (i.e. insulin pump)) treatment parameters for patients with diabetes.

15 Claims, 12 Drawing Sheets

Related U.S. Application Data

(60) Provisional application No. 62/454,282, filed on Feb. 3, 2017.

(51) Int. Cl.
| | | |
|---|---|---|
| *A61M 5/142* | (2006.01) | |
| *G16H 10/60* | (2018.01) | |
| *G16H 20/17* | (2018.01) | |
| *G16H 40/67* | (2018.01) | |
| *A61K 38/28* | (2006.01) | |

(52) U.S. Cl.
CPC .............. *G16H 10/60* (2018.01); *G16H 20/17* (2018.01); *G16H 40/67* (2018.01); *A61K 38/28* (2013.01); *A61M 2205/3303* (2013.01); *A61M 2205/3584* (2013.01); *A61M 2205/502* (2013.01); *A61M 2205/52* (2013.01)

(56) References Cited

U.S. PATENT DOCUMENTS

| | | | |
|---|---|---|---|
| 8,954,373 | B2 | 2/2015 | Atlas et al. |
| 10,169,540 | B2 | 1/2019 | Köhler et al. |
| 10,525,199 | B2 | 1/2020 | Guerrini |
| 10,722,650 | B2* | 7/2020 | Duke .................... G16H 20/10 |
| 11,024,429 | B2 | 6/2021 | Patek et al. |
| 11,179,517 | B2* | 11/2021 | Patek ................ A61M 5/14244 |
| 2003/0163223 | A1 | 8/2003 | Blomquist |
| 2005/0177398 | A1 | 8/2005 | Watanabe et al. |
| 2008/0201325 | A1 | 8/2008 | Doniger et al. |
| 2008/0319384 | A1 | 12/2008 | Yodfat et al. |
| 2009/0163793 | A1 | 6/2009 | Koehler et al. |
| 2010/0121170 | A1 | 5/2010 | Rule |
| 2011/0208156 | A1 | 8/2011 | Doyle et al. |
| 2012/0109047 | A1 | 5/2012 | Yodfat et al. |
| 2012/0220939 | A1 | 8/2012 | Yodfat et al. |
| 2014/0258190 | A1 | 9/2014 | Doniger et al. |
| 2015/0025495 | A1 | 1/2015 | Peyser |
| 2015/0190098 | A1 | 7/2015 | Patek et al. |
| 2015/0273147 | A1 | 10/2015 | Duke et al. |
| 2016/0038673 | A1 | 2/2016 | Morales |
| 2016/0089494 | A1 | 3/2016 | Guerrini |
| 2016/0158471 | A1 | 6/2016 | Fink et al. |
| 2017/0332952 | A1* | 11/2017 | Desborough .......... G16H 20/17 |

FOREIGN PATENT DOCUMENTS

| | | |
|---|---|---|
| CN | 101461969 A | 6/2009 |
| CN | 102500013 A | 6/2012 |
| CN | 102667787 A | 9/2012 |
| CN | 103418053 A | 12/2013 |
| CN | 105339943 A | 2/2016 |
| CN | 106326651 A | 1/2017 |
| JP | 2004000555 A | 1/2004 |
| JP | 2004024699 A | 1/2004 |
| JP | 2010519623 A | 6/2010 |
| JP | 2010531707 A | 9/2010 |
| KR | 10-20120102048 A | 9/2012 |
| WO | 2015021441 A1 | 2/2015 |

OTHER PUBLICATIONS

Office Action (Examination Report No. 1) dated Jul. 15, 2022, by the Australian Patent Office in corresponding Australian Patent Application No. 2018215533. (3 pages).

First Office Action dated Apr. 16, 2021, by the Chinese Patent Office in corresponding Chinese Patent Application No. 201880017688.0, and an English Translation of the Office Action. (19 pages).

Office Action dated Jan. 19, 2021, by the Canadian Patent Office in corresponding Canadian Patent Application No. 3,052,457. (5 pages).

The extended European Search Report dated Oct. 20, 2020, by the European Patent Office in corresponding European Application No. 18748144.5. (14 pages).

Vereshchetin et al., "Mealtime Correction Insulin Advisor for CGM-informed Insulin Pen Therapy," 2013 American Control Conference {ACC), 2013, pp. 2917-2922.

Office Action (Communication) dated Oct. 26, 2023, by the European Patent Office in corresponding European Patent Application No. 18 748 144.5. (8 pages).

Office Action issued on Feb. 2, 2024, by the Chinese Patent Office in corresponding Chinese Patent Application No. 202210379262.8, and an English Translation of the Office Action. (10 pages).

\* cited by examiner

| Actual Time of Injection | Injection Amount (U) |
|---|---|
| 9/21/15 6:00 | 19.6 |
| 9/22/15 6:00 | 19.6 |
| 9/24/15 12:00 | 19.6 |
| 9/27/15 6:00 | 19.6 |
| 9/28/15 6:00 | 19.6 |
| 9/29/15 6:00 | 19.6 |
| 10/1/15 2:00 | 19.6 |
| 10/2/15 6:00 | 19.6 |

FIG. 4

METHOD, SYSTEM, AND COMPUTER READABLE MEDIUM FOR CONTROLLING INSULIN DELIVERY USING RETROSPECTIVE VIRTUAL BASAL RATES

CROSS-REFERENCE TO RELATED APPLICATIONS AND CLAIM OF PRIORITY

This application claims the benefit of U.S. Provisional Application Ser. No. 62/454,282 filed Feb. 3, 2017, under 35 U.S.C. 119(e) and PCT Article 8.

BACKGROUND OF THE INVENTION

In health, blood glucose (BG) is tightly controlled by a hormonal network that includes the gut, liver, pancreas, and brain, ensuring stable fasting BG levels (~80-100 mg/dl) and transient postprandial glucose fluctuations. Diabetes is a combination of disorders characterized by absent or impaired insulin action, resulting in hyperglycemia. Intensive insulin and oral medication treatment to maintain nearly normal levels of glycemia markedly reduces chronic complications in both Type 1 and Type 2 diabetes, but may cause a risk of potentially life-threatening severe hypoglycemia (SH). This SH results from imperfect insulin replacement, which may reduce warning symptoms and hormonal defenses.

Prior to the 1970s, intensive therapy was defined primarily by multiple daily injections (MDI) of insulin, in which the timing and dosage of each injection was chosen to satisfy insulin requirements throughout the day. Over the years MDI therapy has evolved to include the use of both long-acting insulin (e.g. glargine and detemir) given once or twice daily to satisfy insulin requirements between meals and rapid-acting insulin (e.g. lispro and aspart) to cover insulin requirements associated with meals. Many patients find insulin pens to be a convenient mechanism for manual injections of insulin.

An insulin pen consists of a vial of insulin (either long- or rapid acting insulin), hypodermic needle, and a plunger mechanism integrated into a single pen-like form factor, allowing patients to "dial in" the desired dose. In the 1970s, continuous subcutaneous insulin infusion (CSII, a.k.a insulin pump) therapy became a viable alternative to MDI. While CSII therapy is associated with lower glycosylated hemoglobin (HbA1c), lower glycemic variability, and lower incidence of hypoglycemia, many patients remain on MDI due in part to the higher cost associated with insulin pumps and the need for trained supervision of the use of insulin pumps.

The technology for BG sensing has similarly undergone a transformation over the years. Self-monitoring of blood glucose (SMBG), involving the use of a lancet and chemical test strip for each sample, arrived in the 1960s, replacing the relatively crude and non-specific methods of BG urinalysis. SMBG is to this day the primary mechanism for assessing BG for treatment, often used to make corrections to mealtime insulin doses based on out-of-range BG levels. Within the last decade, continuous glucose monitoring (CGM), with BG samples every five minutes or less, has become available to patients as an adjunct to SMBG, giving patients a more complete understanding of glycemic variability throughout the day. The introduction of CGM led many research groups to work toward the development of a safe and effective "artificial pancreas" in which CGM informs closed-loop adjustment of CSII insulin delivery in real time.

While many patients would benefit from the reduced burden of control that would come with an artificial pancreas, such devices can be expensive and would appeal mainly to technologically savvy patients. Also, many patients may rather remain in control themselves, desiring only CGM-informed advice about insulin injections rather than automation.

Systems for real time advice to insulin pump users have been investigated in Patek et al., "Correction insulin advisory system based on meal behavioral profiles," IFAC 18th World Congress, 2011, pp. 8354-8359, focusing on optimal between-meal correction bolus recommendations on demand, which is incorporated by reference herein.

Vereshchetin et al., "Mealtime Correction Insulin Advisor for CGM-Informed Insulin Pen Therapy," Proceedings of the American Control Conference (ACC), June 2013, also incorporated by reference herein, first explored the opportunity to provide CGM-informed advice to MDI patients at mealtimes. Specifically, as illustrated in FIG. 12, a "smart" insulin pen 1201 can provide real time advice to a user about corrections to mealtime rapid-acting insulin/glargine boluses 1202 based on CGM readings received by a wireless glucometer 1203 from a subcutaneously implanted CGM sensor 1204 (in addition to a SMBG reading) and (ii) an internal representation of the pharmacokinetic characteristics of long-acting insulin. Vereshchetin et al. sought to determine the extent to which MDI patients could benefit from algorithmic support for computing optimal correction boluses, for possible development of an integrated insulin pen/CGM receiver for the smart insulin pen platform.

Vereshchetin et al. presented a nominal model of the pharmacokinetic (PK) properties of once-daily long-acting insulin, incorporated into a computer simulation environment for MDI therapy of Type 1 diabetes, and, based on the pharmacokinetic model, introduced the notion of a "virtual basal rate" profile associated with daily long-acting insulin injections, facilitating the estimation of the patient's metabolic state via Kalman filtering. Vereshchetin et al. then computed correction bolus recommendations for mealtime rapid-acting boluses in MDI therapy using this metabolic state estimate. The correction advisor was evaluated for an in silico Type 1 population whose self-treatment strategies achieve an HbA1c of 7.98% on average (with a standard deviation of 0.52), and the algorithm results in a reduction of over one percent saturation without significantly increasing the risk of hypoglycemia, even under +/−25% variation in the absorption parameter $k_{d0}$. The in silico results suggested that the combination of CGM with MDI can be very effective in improving glycemic control for patients with Type 1 diabetes, extracting many of the benefits of fully closed-loop pump oriented systems (e.g. the artificial pancreas).

To obtain the in silico results a rough model of self-treatment for a population of Type 1 subjects was constructed, in which each model patient was assigned (i) a daily long-acting insulin dose and (ii) a carbohydrate ratio and correction factor so that the overall group achieves a mean HbA1c of 7.98%. The reference therapy model was then tuned to achieve a reduction in HbA1c, keeping the risk of hypoglycemia as a secondary criterion.

At mealtimes the patient would compute a carb-related bolus by applying his or her carbohydrate ratio (CR) to an estimate of the size of the meal. However, instead of using his/her correction factor, an insulin correction was computed, which adjusts for the patient's current state (e.g. high or low BG at the time of the meal), by minimizing the objective function $$F(u) = u'Ru + \sum_{k=\kappa}^{\kappa+N} (C\breve{x}(k) - \Delta)' Q (C\breve{x}(k) - \Delta)$$

where κ is the stage in which the patient intends to deliver a mealtime bolus of rapid-acting insulin, N is the planning horizon (e.g., N=72 five minute intervals, i.e. 6 hours), Q and R are positive semidefinite and definite weighting matrices, respectively, Δ is a desired BG offset, and $\{\breve{x}(k)\}_{k=\kappa}^{\kappa+N}$ is governed by $$\breve{x}(\kappa) = \hat{x}(\kappa)$$
$$\breve{x}(\kappa+1) = A\breve{x}(\kappa) + Bu + Bu^{LA}(\kappa)$$
$$\breve{x}(\kappa+2) = A\breve{x}(\kappa+1) + Bu^{LA}(\kappa+1)$$
$$\vdots$$
$$\breve{x}(\kappa+N) = A\breve{x}(\kappa+N-1) + Bu^{LA}(\kappa+N-1).$$

In the above that the correction insulin bolus u is applied only in stage κ, and the only other variation in insulin is due to the pharmacokinetic (PK) characteristics of the long-acting insulin injected at k=0. x(κ) is taken to be the Kalman filter estimate $\hat{x}(\kappa)$ of the patient's state.

As shown in FIG. 13, that mealtime correction bolus algorithm was devised as follows. Suppose that the patient is interested in advice about an optimal correction bolus at discrete time κ. The first step of the algorithm was to compute an estimate $\hat{x}(\kappa)$ of the patient's metabolic state based on both CGM/SMBG measurements and the patient's virtual basal deviation $u^{LA}$ rate up to κ. The CGM input to the Kalman filter is relative to an algorithm parameter $\overline{BG}$, which could be initialized based on patient's daily average blood glucose concentration and adjusted thereafter as the patient achieves better glycemic outcomes. In practice, the mealtime SMBG sample would be used to adjust the CGM history (to eliminate the effect of sensor drift) prior to computing the estimate $\hat{x}(\kappa)$. The next step of the algorithm was to compute an LQ (linear quadratic) optimal discrete correction bolus based on (i) the current estimate of the patient's metabolic state, (ii) future values of the virtual basal rate signal $u^{LA}$, and (iii) a desired offset Δ. Offset Δ allows the patient to compensate for a poorly titrated long acting insulin dose, such that if the long-acting dose is too low (resulting in a high average BG), then correction boluses can be designed to achieve a BG offset that applies at least for the duration of action for the correction bolus. The parameters q and Δ can be regarded as tuning parameters for the algorithm.

SUMMARY OF THE INVENTION

According to one aspect of the present invention, a method, system, and computer readable medium are provided for the construction of equivalent insulin pump retrospective virtual basal rates from planned insulin injections according to a virtual basal rate profile developed for a patient, and a database of historical insulin injections (i.e. basal injections actually administered by the patient), providing a unified framework for analysis, design, optimization, and adaptation of MDI (multiple daily injections) and CSII (continuous subcutaneous insulin infusion (i.e. insulin pump) treatment parameters for patients with diabetes.

Another aspect of the present invention provides a method, system, and computer readable medium for virtualization of retrospective virtual basal rates from planned and historical insulin delivery.

BRIEF DESCRIPTION OF THE DRAWINGS

FIG. 4 is a table of a historical record of insulin injections as recorded by a user;

DETAILED DESCRIPTION OF EXEMPLARY EMBODIMENTS OF THE INVENTION

According to embodiments of the present invention, the pharmacokinetic (PK) properties of insulin (especially medium- and long-acting insulin products) are used to construct a planned CSII virtual basal rate profile, and the actual historical record of insulin injections by the patient are used to construct a retrospective virtual basal rate. The units of insulin to be injected or administered to a patient in accordance with the planned injections according to the virtual basal rate profile are then modified according to the retrospective virtual basal rate, providing a more accurate dosing for the patient based on the patient's actual history of insulin administration.

Virtual Basal Rate Profile

Based on a pattern of consistent daily injections (including the case of multiple injections at different times of the day), the system (and related systems):
uses the PK properties of insulin to infer the limiting continuous pattern of plasma insulin concentration over a 24-hour cycle, and then uses the PK properties of rapid-acting insulin delivered via CSII to determine the continuous CSII basal rate profile that would lead to the same pattern of plasma insulin concentration over a 24-hour cycle.

Figure 2:
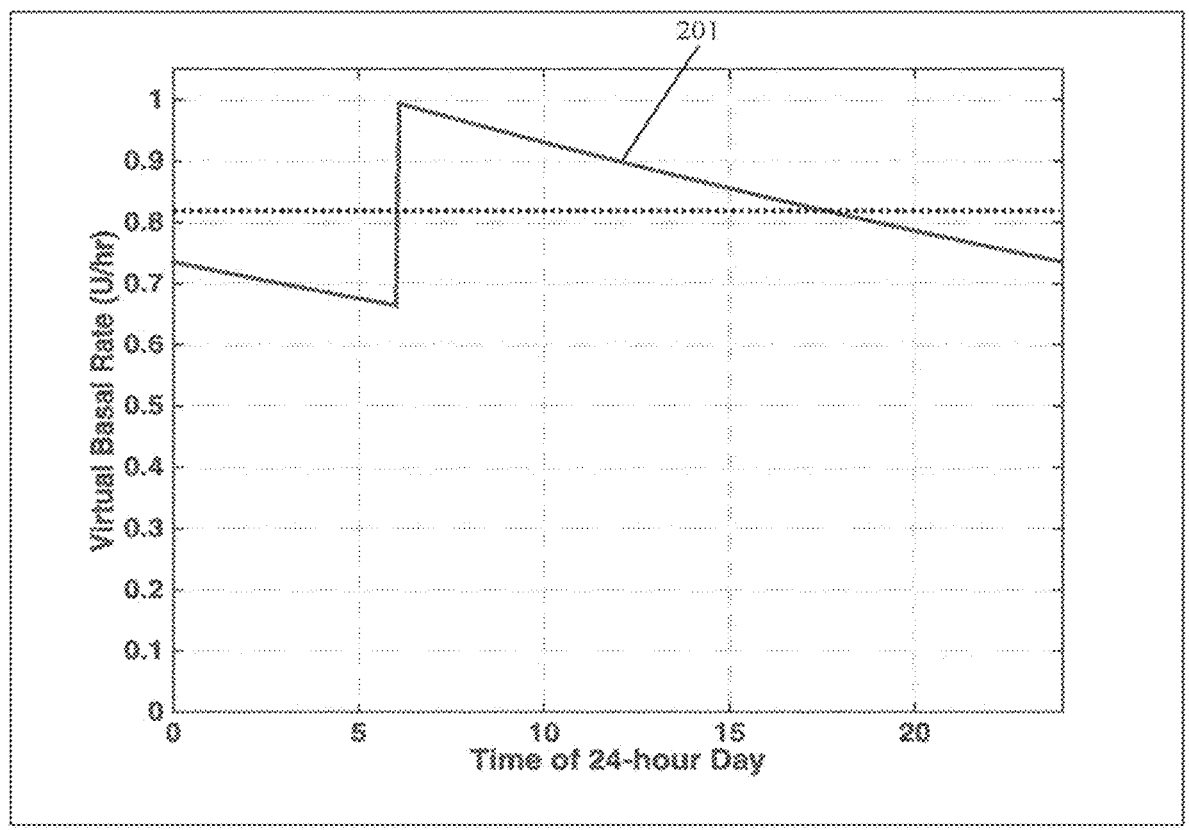
FIG. 2 is a graph of a virtual basal rate profile for a planned daily insulin injection over a 24 hour period.

FIG. 2 illustrates the virtual basal rate profile 201 that results from planned daily injection of 19.6 units of insulin glargine at 06:00 AM. The units of the y-axis of the plot are U/hour. Note that the time-average value of the virtual basal rate profile at 0.8167 U/hr (dashed line) matches the fact that 19.6 units of insulin are planned for the 24-hour day. The variability of the virtual basal rate profile around this average value is the result of the PK properties of insulin glargine, which (despite the popular conceptual view) are not flat over a 24-hour period, but rather describe a measurable rise time and decay from peak concentration throughout the day.

Figure 1:
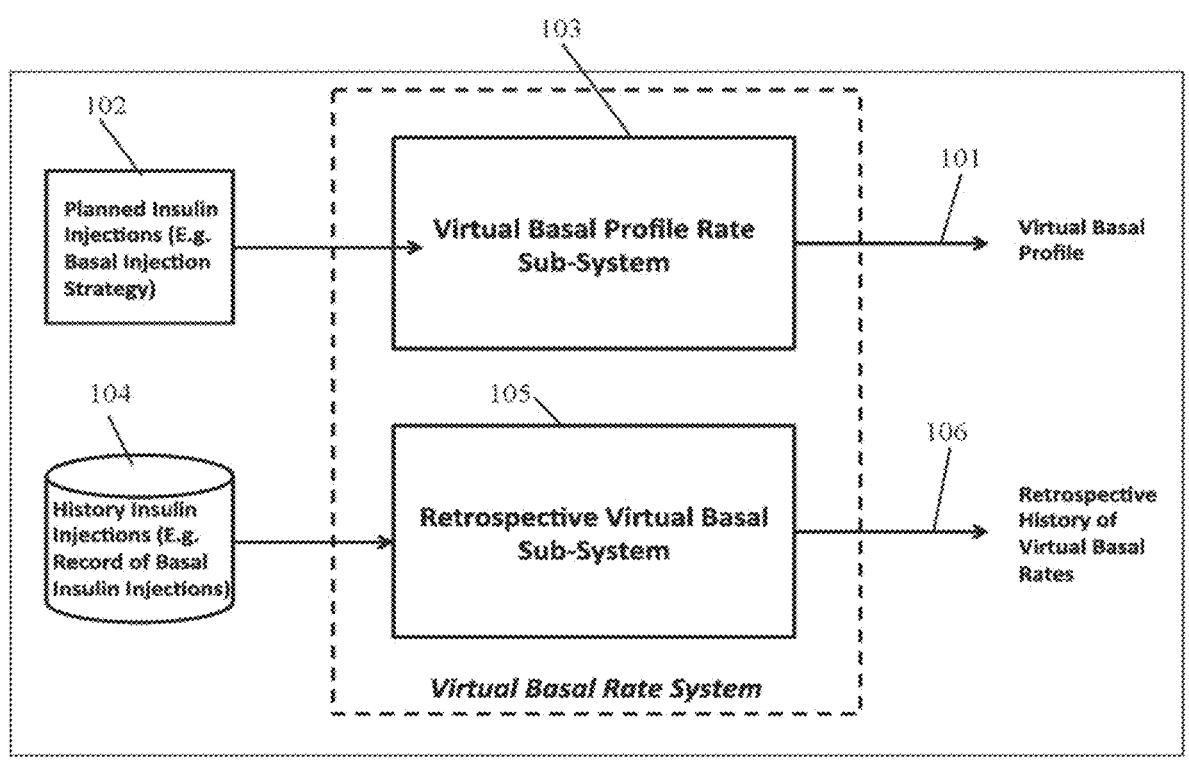
FIG. 1 is a block diagram of a virtual basal rate system in accordance with one aspect of the present invention.

Referring to FIG. 1, the virtual basal rate profiles 101 may be constructed as follows:

1. Given an insulin injection plan 102 the subsystem 103 uses a mathematical model of the PK properties of insulin to infer a steady-state orbit of plasma insulin concentration assuming that the plan is followed precisely infinitely far back in the past:

$$I_{steadystate}(\tau)=F_{steadystate}(\tau;\{J(\sigma)\}_{\sigma=0}^{T_{day}},\theta),\tau \text{ in } [0,T_{day}],$$

where $I_{steadystate}(\tau)$ represents plasma insulin concentration at time $\tau$ in the 24-hour day, based on the planned injections represented by the function $J(\sigma)$ that describes the injections intended at each time $\sigma$ in the 24-hour day represented by the interval $[0, T_{day}]$. Here, $F_{steadystate}$ is the function that describes the steady-state plasma concentrations resulting from the planned daily injections and the specific PK parameters $\theta$ of the insulin type under consideration.

2. Using the PK properties of rapid-acting insulin delivered via CSII insulin pump, the subsystem 103 infers a virtual basal rate profile $\{b(\sigma)\}_{\sigma=0}^{T_{day}}$ that describes the basal infusion pattern whose corresponding steady state pattern of plasma insulin concentration $G_{steadystate}(\tau; \{b(\sigma)\}_{\sigma=0}^{T_{day}}, \theta)$ matches the plasma insulin concentration pattern from the daily injections, i.e.

$$G_{steadystate}(\tau;\{b(\sigma)\}_{\sigma=0}^{T_{day}},\theta)=I_{steadystate}(\tau)$$

for all $\tau$ in $[0, T_{day}]$.

Figure 3:
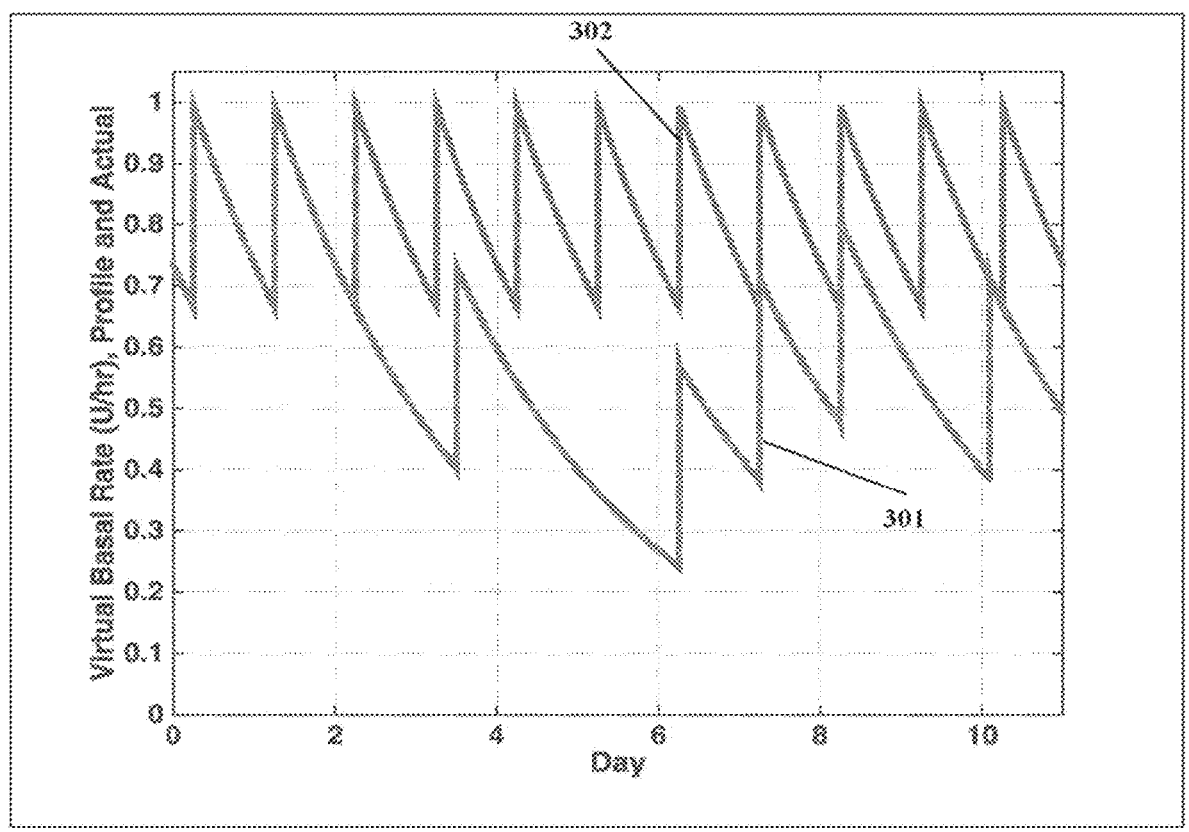
FIG. 3 is a graph of retrospective (historical) virtual basal rates resulting from an actual record of insulin injections, and a virtual basal rate profile from planned injections, showing variations between them as a result of actual patient behavior.

Trace 301 in FIG. 3 illustrates the historical virtual basal rates that result from the record of actual insulin glargine injections, as shown in FIG. 4, over the time period of 9/21/15 to 10/2/15 as an example. In FIG. 3, trace 302 shows the virtual basal rate profile that derives from the planned injection of 19.6 units of insulin at 06:00 AM each day. From FIG. 4 it will be noted that long-acting insulin injections were missed by the patient on the 23rd, 25th, 26th, and the 30$^{th}$. These missing insulin injections result in significant basal rate deviations from the virtual basal rate profile obtained according to the plan. The present invention provides a novel method of quantifying the effect of imprecise insulin delivery that varies from planned injections according to the patient's obtained profile.

Retrospective Virtual Basal Rates

Referring back to FIG. 1, based on a historical record of insulin injections 104 (including the timing and amounts of doses and allowing for the possibility of missing injections over multiple days), the subsystem 105 constructs a retrospective virtual basal rate 106 by:

using the PK properties of insulin to infer the concentration of plasma insulin concentration resulting from the injections over time, and then using the PK properties of rapid-acting insulin delivered via CSII to determine the continuous CSII basal rate profile that would lead to the same historical concentrations of plasma insulin concentration over a 24-hour cycle.

Virtual basal rate profiles may be constructed as follows:

1. Given the record of actual insulin injections over a period of time $$\{J_{hist}(\sigma)\}_{\sigma=0}^{T}{}_{\sigma=0} \text{ for } \sigma \text{ in } [0,T],$$

where T is the length of the time period (typically corresponding to multiple days), the system uses a mathematical model of the PK properties of insulin to infer the plasma insulin concentrations that result from those injections:

$$I_{transient}(\tau)=F_{transient}(\tau;\{J_{hist}(\sigma)\}_{\sigma=0}^{T},\theta,I(0)),\tau \text{ in } [0,T],$$

where $I_{transient}(\tau)$ represents plasma insulin concentration at time $\tau$ in the historical record. Here, $F_{transient}$ is the function that describes the specific (transient) plasma concentrations resulting from the historical injections given (i) the specific PK parameters $\theta$ of the insulin type under consideration and (ii) given the initial plasma insulin concentration $I(0)$. (If the initial plasma insulin concentration is not known, then it can be estimated from the steady state value obtained in the virtual basal rate profile calculation above.)

2. Using the PK properties of rapid-acting insulin delivered via CSII insulin pump, the system infers a virtual historical record of basal rate insulin delivery $\{b(\sigma)\}_{\sigma=0}^{T}$ whose corresponding instantaneous plasma insulin concentrations $G_{transient}(\tau; \{b(\sigma)\}_{\sigma=0}^{T}, \theta, I(0))$ match the plasma insulin concentration pattern from the historical injections, i.e.

$$G_{transient}(\tau;\{b(\sigma)\}_{\sigma=0}^{T},\theta,I(0))=I_{transient}(\tau)$$

for all $\tau$ in $[0, T]$.

Figure 10:
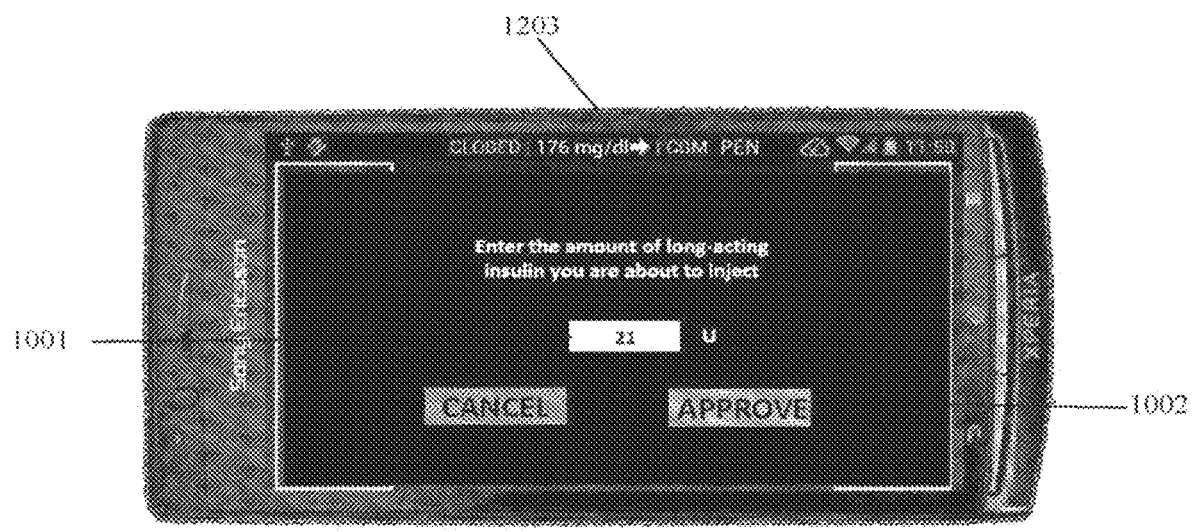
FIGS. 10 and 11 are schematic diagrams of a wireless glucometer used with embodiments of the present present invention.
Figure 11:
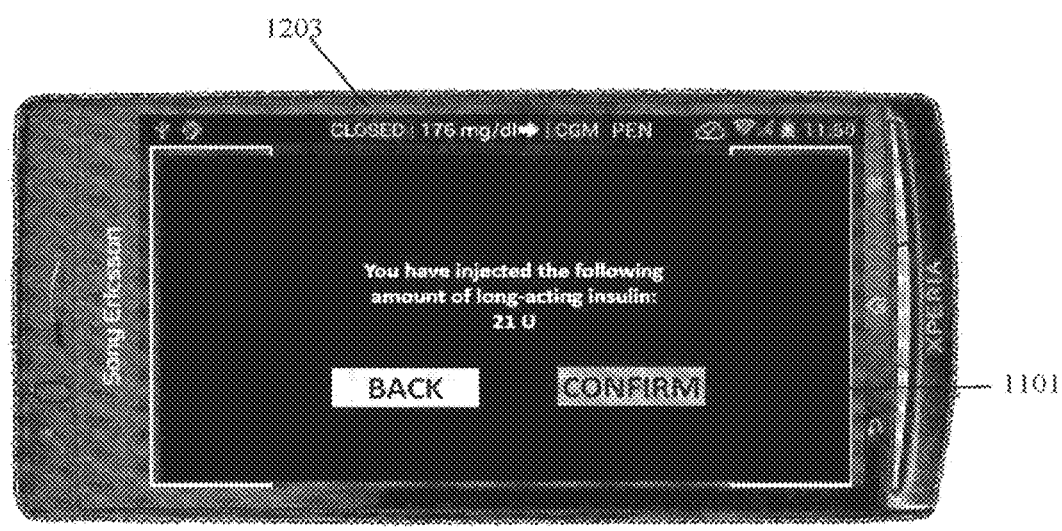
Figure 12:
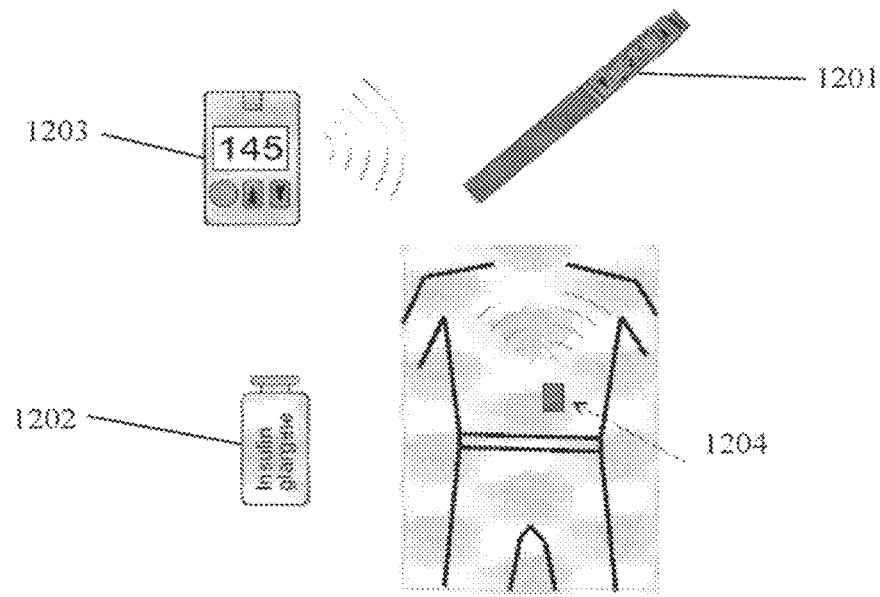
FIG. 12 is a block diagram of a prior art general smart insulin pen system usable with the present invention.
Figure 13:
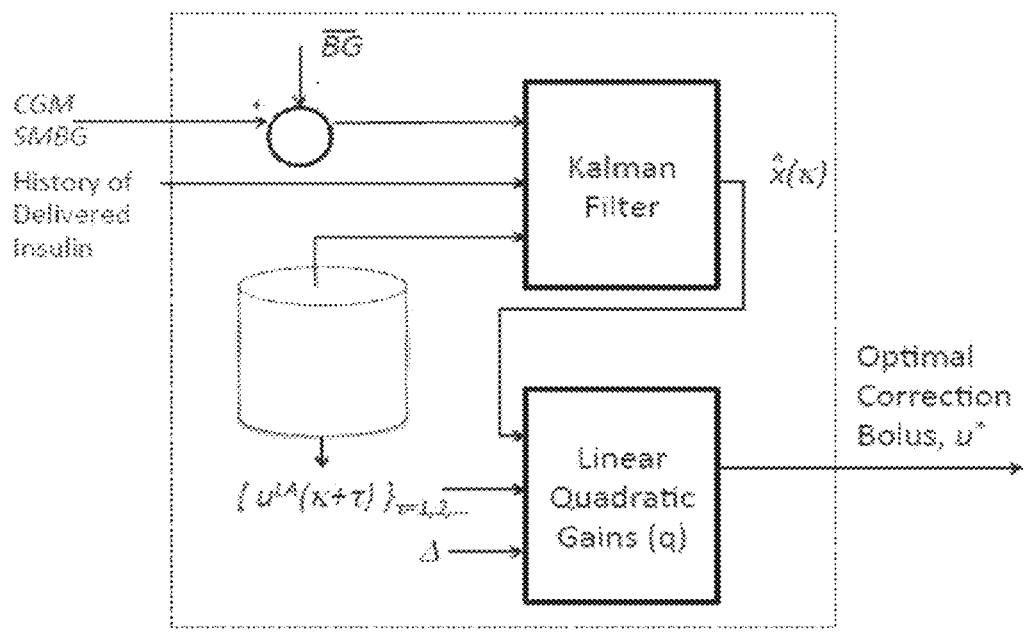
FIG. 13 is a block diagram of a prior art mealtime correction bolus algorithm, which can be used in conjunction with the present invention.

FIG. 10 shows an example of how a user would enter and confirm insulin injections according to the user's basal rate profile. The user enters into input area 1001 on the display of wireless glucometer 1204 the units of insulin about to be injected, and may either approve this amount or cancel the injection by using "cancel" and "approve" touch-sensitive buttons 1002. The glucometer 1203 then displays a screen such as shown in FIG. 11, requesting the user to confirm that the indicated insulin dose was injected, using touch-sensitive buttons 1101. Upon confirmation the date and time along with the units of insulin injected are recorded in the database 104.

An aspect of the present invention may provide a number of novel and nonobvious features, elements and characteristics, as well as advantages, as discussed below. For example, an advantage of basal virtualization is that it permits the application of retrospective methods (e.g. treatment optimization) and on-line methods (e.g. real-time estimation and control of diabetes) that were originally developed for insulin pump users to the large population of diabetes patients on multiple daily injections (MDI) therapy.

An aspect of various embodiments of the present invention may be utilized for a number of products and services, such as but not limited thereto, as discussed below. Basal virtualization can be used in any retrospective or real-time application that normally assumes insulin delivery via CSII (insulin pump). An aspect of an embodiment of the present invention provides for the use of basal virtualization in (i)

treatment optimization where basal insulin requirements are achieved via daily manual injections of long-acting insulin and (ii) in systems for real-time treatment advice (e.g. bolus or exercise advice) where basal virtualization contributes to the best estimate of patient's metabolic state. The retrospective applications identified above would naturally fit within a "cloud" analytic framework, whereas the real-time applications may take form as a hybrid of "cloud" and embedded computation.

An aspect of an embodiment of the present may be used in, but not limited to, various "Cloud Analytics" applications in the treatment of diabetes (Type 1 and Type 2).

Figure 5:
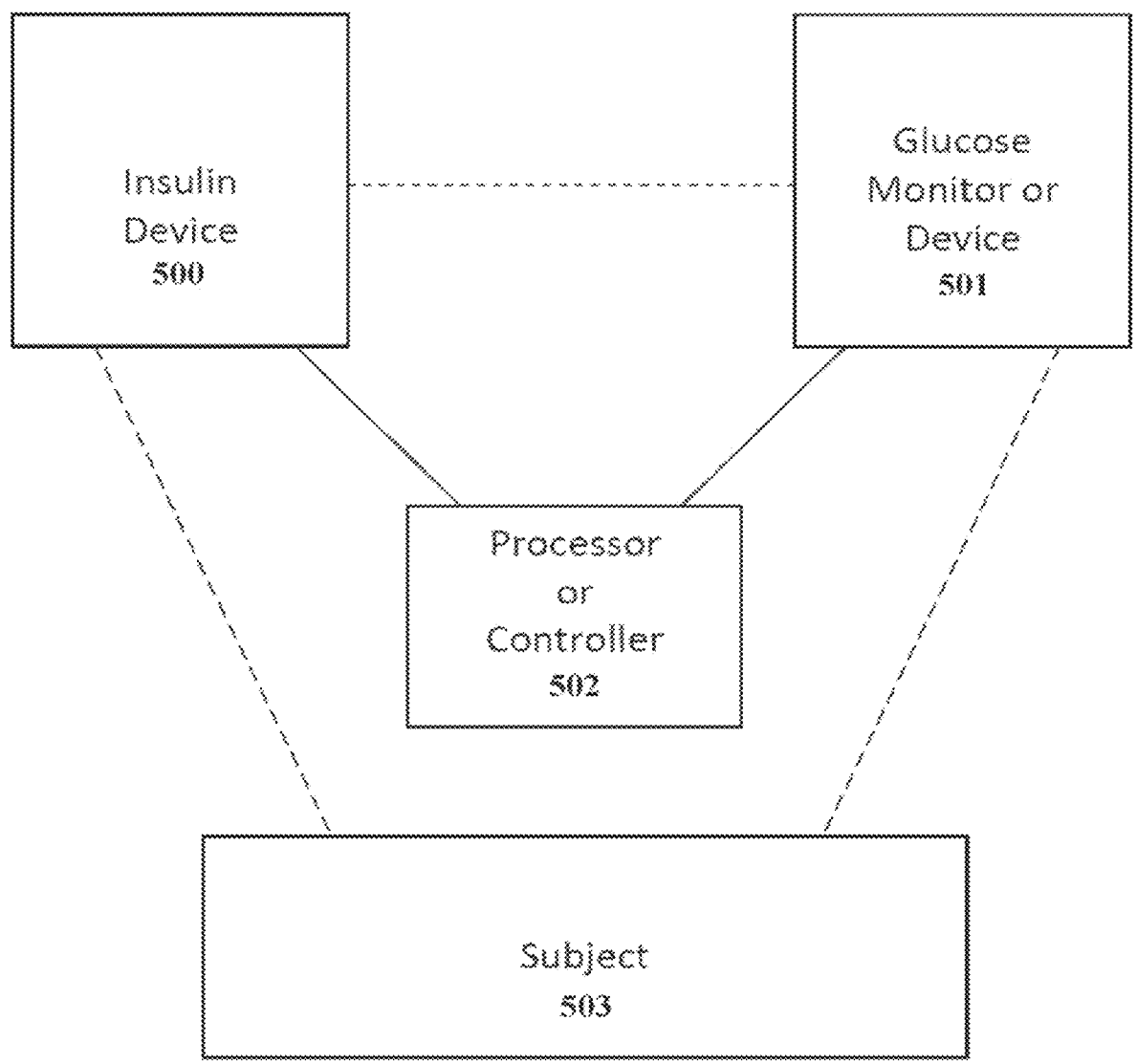
FIG. 5 is a block diagram of an example of a machine upon which one or more aspects of embodiments of the present invention can be implemented.

FIG. 5 is a high level functional block diagram of an embodiment of the present invention, or an aspect of an embodiment of the present invention shown in FIG. 1, whereby the system shown in FIG. 1 can be implemented in the processor or controller 502 of FIG. 5.

As shown in FIG. 5, a processor or controller 502 communicates with glucose monitor or device 501, and optionally insulin device 500. The glucose monitor or device 501 communicates with the subject 103 to monitor glucose levels of the subject 103. The processor or controller 102 is configured to perform the required calculations. Optionally, the insulin device 500 communicates with the subject 503 to deliver insulin to the subject 503. The processor or controller 502 is configured to perform the required calculations. The glucose monitor 501 and the insulin device 500 may be implemented as a separate device or as a single device. The processor 502 can be implemented locally in the glucose monitor 501, the insulin device 500, or a standalone device (or in any combination of two or more of the glucose monitor, insulin device, or a stand along device). The processor 502 or a portion of the system can be located remotely such that the device is operated as a telemedicine device.

Figure 6A:
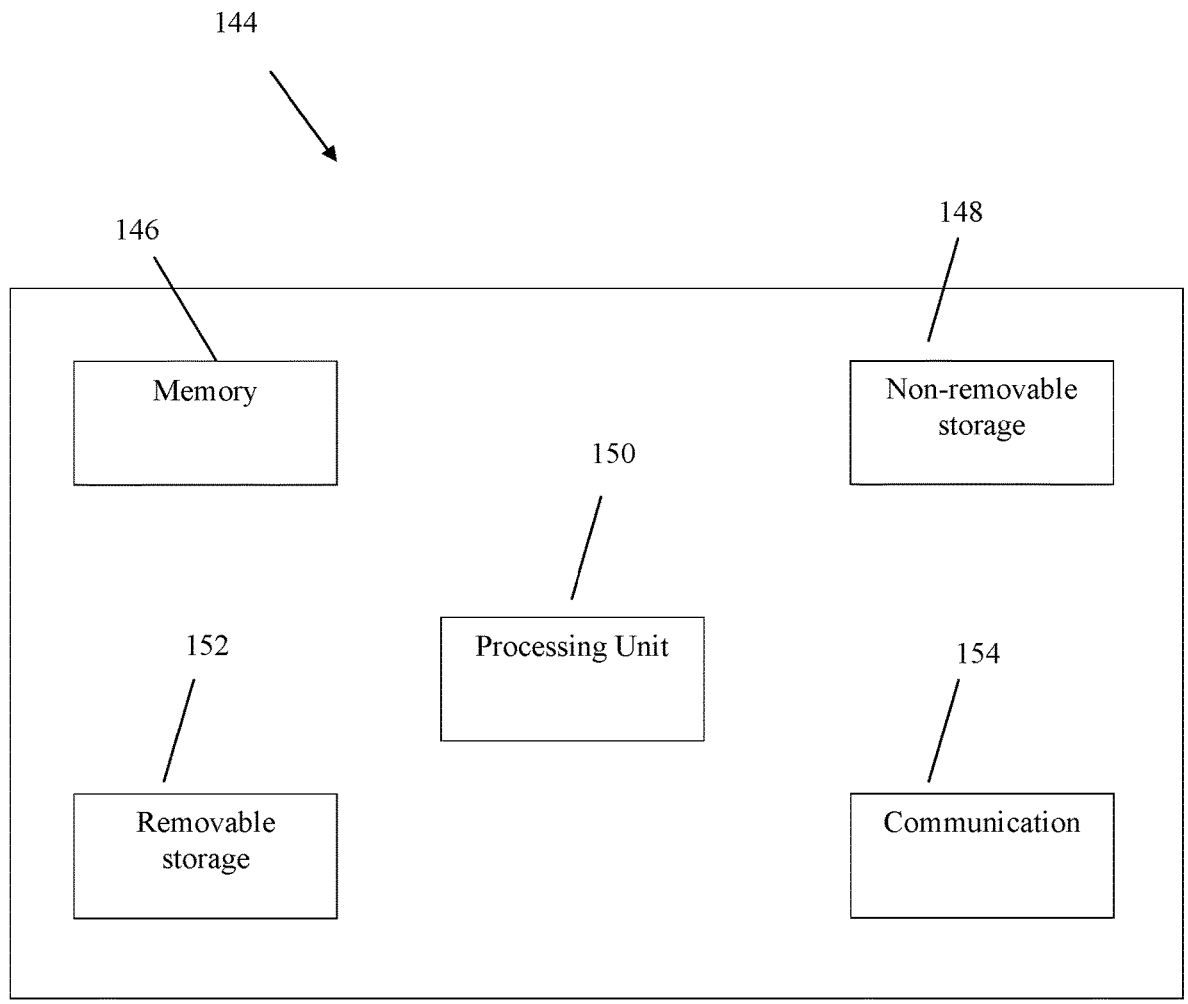
FIG. 6A is a block diagram of a computing device upon which one or more aspects of embodiments of the invention can be implemented.

Referring to FIG. 6A, in its most basic configuration, a computing device 144 (such as processor 502 shown in FIG. 5) typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 6B:
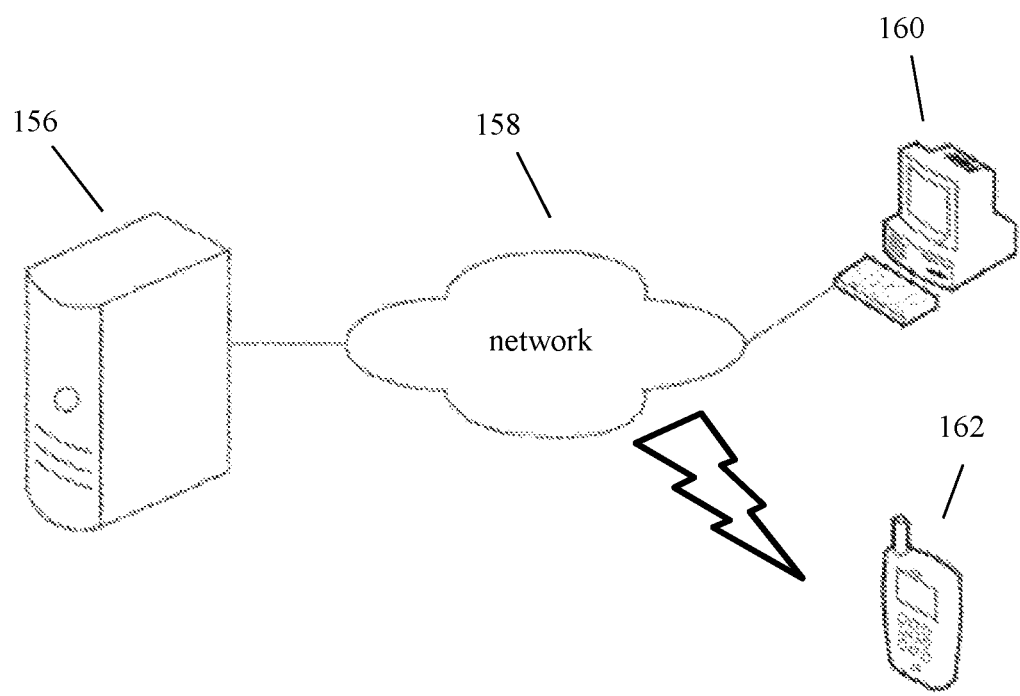
FIG. 6B illustrates a network system upon which one or more aspects of embodiments of the invention can be implemented.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. As a way of example, FIG. 6B illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). In an embodiment, it should be appreciated that the module listed as 156 may be glucose monitor device. In an embodiment, it should be appreciated that the module listed as 156 may be a glucose monitor device (or glucose meter) and/or an insulin device. Any of the components shown or discussed with FIG. 6B may be multiple in number. The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

Figure 7:
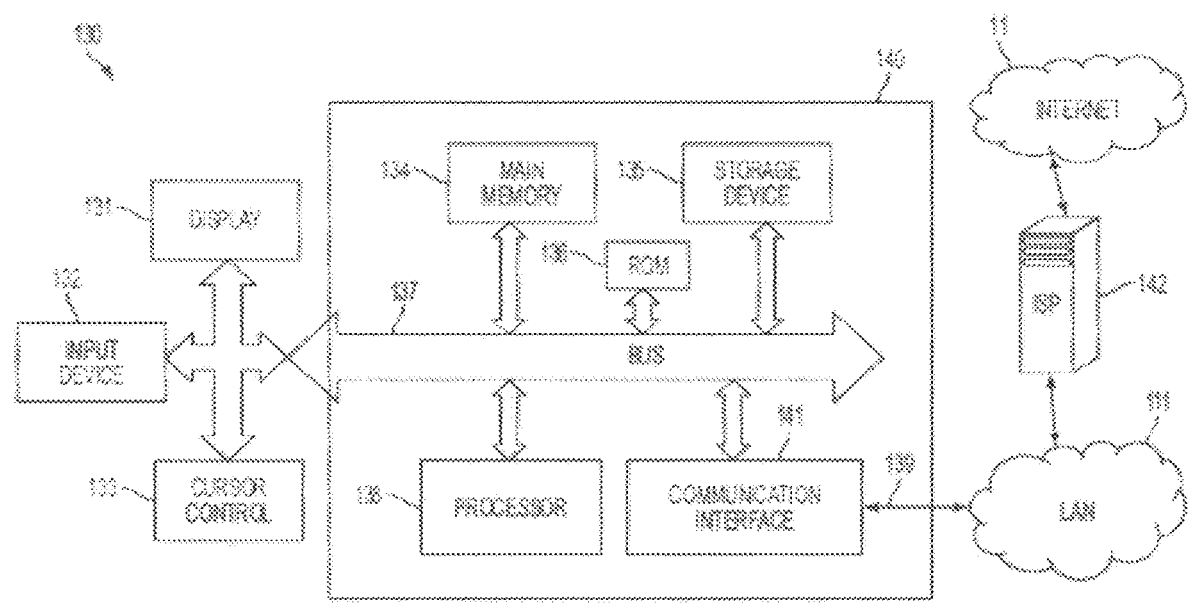
FIG. 7 illustrates a system in which one or more embodiments of the invention can be implemented using a network, or portions of a network of computers.

FIG. 7 is a block diagram that illustrates a system 130 including a computer system 140 and the associated Internet 11 connection upon which the embodiments described herein may be implemented. Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 7. The system 140 may be used as a portable electronic device such as a notebook/laptop computer, a media player (e.g., MP3 based or video player), a cellular phone, a Personal Digital Assistant (PDA), a glucose monitor device, an insulin delivery device, an image processing device (e.g., a digital camera or video recorder), and/or any other handheld computing devices, or a combination of any of these devices. Note that while FIG. 7 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 7 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments of the invention are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (Feb. 20, 2004), which is incorporated in its entirety for all purposes as if fully set forth herein.

Wireless links may also be implemented. In any such implementation, communication interface 141 sends and receives electrical, electromagnetic or optical signals that carry digital data streams representing various types of information. Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information. A received code may be executed by processor 138 as it is received, and/or stored in storage device 135, or other non-volatile storage for later execution. In this manner, computer system 140 may obtain application code in the form of a carrier wave.

The concept of method and system for virtualization of virtual basal rates from planned and historical insulin delivery have been developed and disclosed herein; and may be implemented and utilized with the related processors, networks, computer systems, internet, and components and functions according to the schemes disclosed herein.

Figure 8:
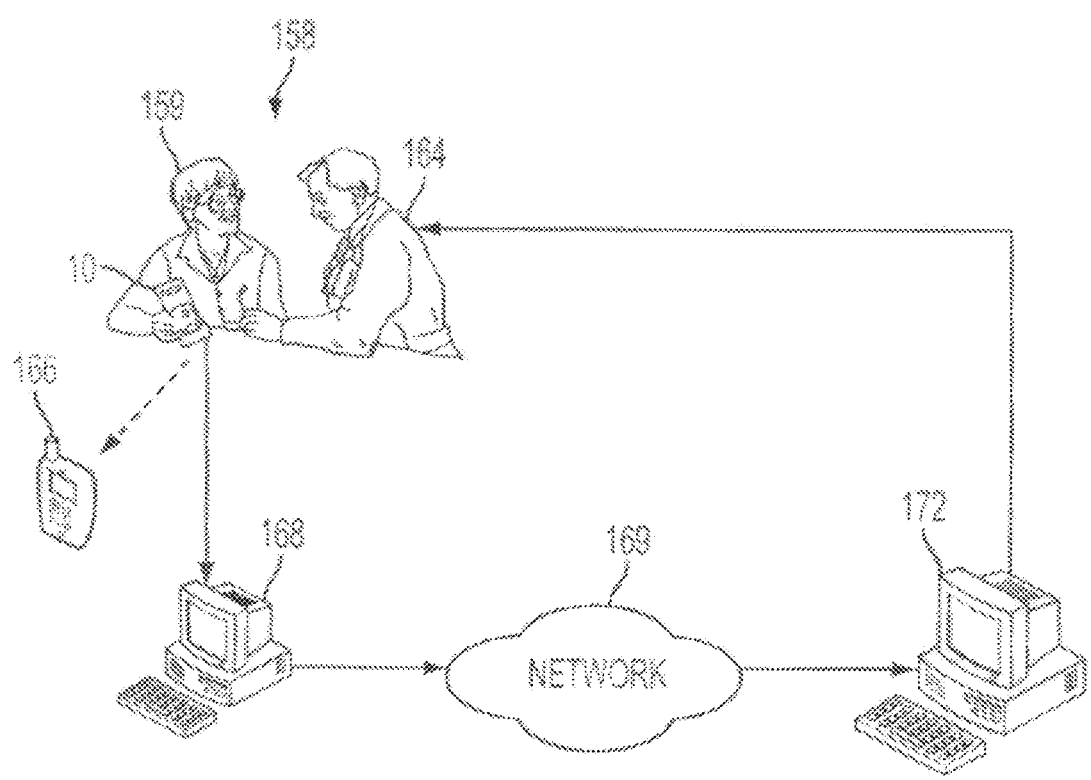
FIG. 8 illustrates a system in which one or more embodiments of the invention can be implemented using a network, or portions of a network of computers.

FIG. 8 illustrates a system in which one or more embodiments of the invention can be implemented using a network, or portions of a network or computers, although the glucose device of the present invention may be practiced without a network.

FIG. 8 diagrammatically illustrates an exemplary system in which examples of the invention can be implemented. In an embodiment the glucose monitor or glucose meter (and/or insulin pump) may be implemented by the subject (or patient) locally at home or other desired location. However, in an alternative embodiment it may be implemented in a clinic setting or assistance setting. For instance, referring to FIG. 8, a clinic setup 158 provides a place for doctors (e.g. 164) or clinician/assistant to diagnose patients (e.g. 159) with diseases related with glucose and related diseases and conditions. A glucose monitoring device 10 can be used to monitor and/or test the glucose levels of the patient—as a standalone device. It should be appreciated that while only glucose monitor device 10 is shown in the figure, the system of the invention and any component thereof may be used in the manner depicted by FIG. 8. The system or component may be affixed to the patient or in communication with the patient as desired or required. For example the system or combination of components thereof—including a glucose monitor device 10 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Examples of the invention can also be implemented in a standalone computing device associated with the target glucose monitoring device. An exemplary computing device (or portions thereof) in which examples of the invention can be implemented is schematically illustrated in FIG. 6A.

Figure 9:
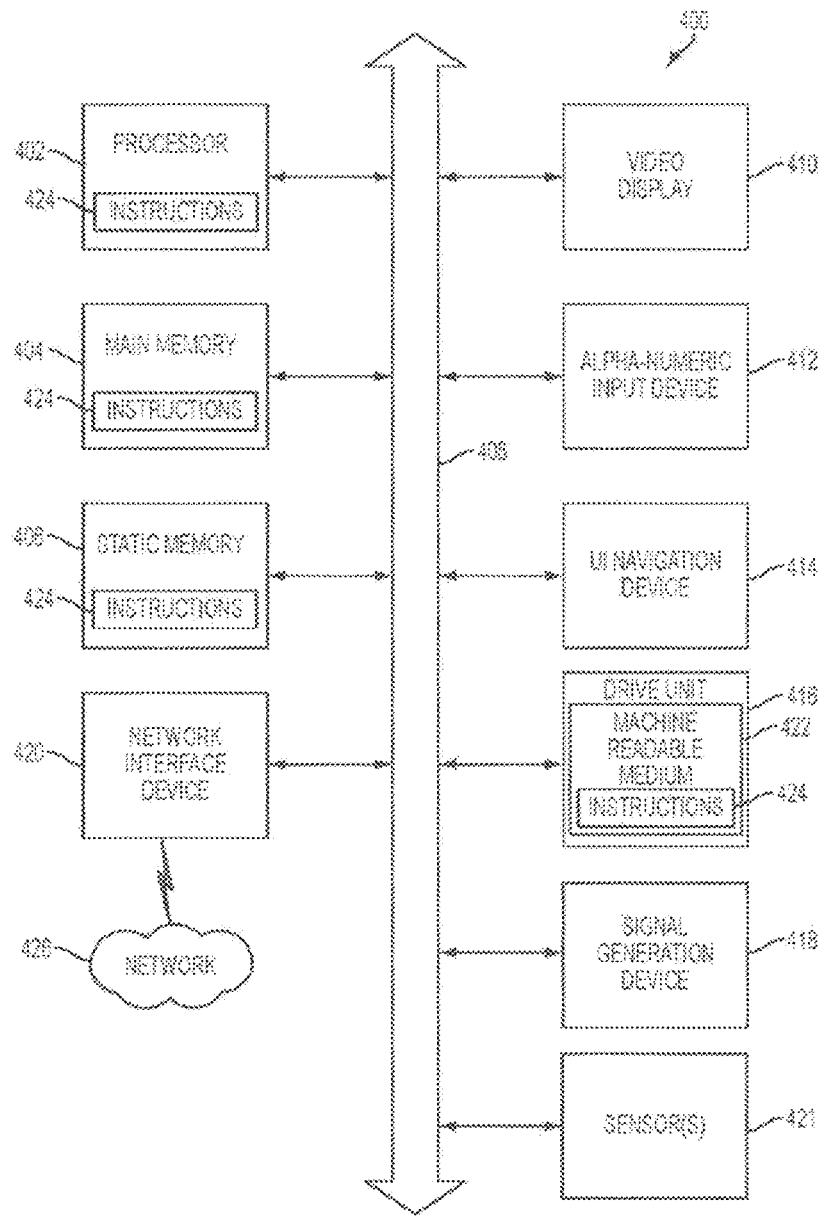
FIG. 9 illustrates a block diagram of an example machine 400 upon which one or more embodiments of the present invention can be implemented.

FIG. 9 is a block diagram illustrating an example of a machine upon which one or more aspects of embodiments of the present invention can be implemented.

FIG. 9 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 410, input device 412 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as) WiMax®, peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is descried herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A device for delivery of insulin, the device comprising:
   a processor configured to calculate an amount of insulin to be administered based on at least in part a retrospective virtual basal rate determined from a historical record of insulin amounts delivered and a blood glucose measurement, and
   wherein the retrospective virtual basal rate is obtained by matching a plasma insulin concentration pattern inferred from a mathematical model of a pharmacokinetic property of insulin in conjunction with the historical record of insulin amounts delivered, to a virtual record of basal rate insulin delivery inferred from a mathematical model of the pharmacokinetic property of rapid-acting insulin delivered.

2. The device of claim 1, wherein the processor is part of or in communication with a handheld or portable electronic device, a cell phone, a computer, glucose monitor device, or an insulin device.

3. The device of claim 1, wherein the processor is configured to receive the blood glucose measurement.

4. The device of claim 1, wherein the blood glucose measurement is a self-monitoring blood glucose (SMBG) measurement.

5. The device of claim 1, wherein the blood glucose measurement is a continuous glucose monitor (CGM) measurement.

6. A method for delivery of insulin, the method comprising:
   calculating an amount of insulin to be administered based on at least in part a retrospective virtual basal rate determined from a historical record of insulin amounts delivered and a blood glucose measurement, and
   wherein the retrospective virtual basal rate is obtained by matching a plasma insulin concentration pattern inferred from a mathematical model of a pharmacokinetic property of insulin in conjunction with the historical record of insulin amounts delivered, to a virtual record of basal rate insulin delivery inferred from a mathematical model of the pharmacokinetic property of rapid-acting insulin delivered.

7. The device of claim 6, wherein the processor is part of or in communication with a handheld or portable electronic device, a cell phone, a computer, glucose monitor device, or an insulin device.

8. The device of claim 6, wherein the processor is configured to receive the blood glucose measurement.

9. The device of claim 6, wherein the blood glucose measurement is a self-monitoring blood glucose (SMBG) measurement.

10. The device of claim 6, wherein the blood glucose measurement is a continuous glucose monitor (CGM) measurement.

11. A device for delivery of insulin, the device comprising:
    a processor configured to calculate an amount of insulin to be administered based on at least in part a retrospective virtual basal rate determined from a historical record of insulin amounts delivered and a blood glucose measurement, wherein the processor:
    infers a history of insulin concentration based on pharmacokinetic (PK) properties of insulin;
    constructs a virtual basal rate profile, based on PK properties of insulin actually delivered, that provides a pattern of insulin concentration that matches with the inferred history of insulin concentration;
    infers concentration of plasma insulin, based on PK properties of insulin actually delivered, and constructs a retrospective virtual basal rate that provides a concentration of plasma insulin that matches with the inferred concentration of plasma insulin; and
    uses the retrospective virtual basal rate to calculate the amount of insulin.

12. The device of claim 11, wherein the processor is part of or in communication with a handheld or portable electronic device, a cell phone, a computer, glucose monitor device, or an insulin device.

13. The device of claim 11, wherein the processor is configured to receive the blood glucose measurement.

14. The device of claim 11, wherein the blood glucose measurement is a self-monitoring blood glucose (SMBG) measurement.

15. The device of claim 11, wherein the blood glucose measurement is a continuous glucose monitor (CGM) measurement.

* * * * *